US00PP29977P3

(12) United States Plant Patent
Hai

(10) Patent No.: US PP29,977 P3
(45) Date of Patent: Dec. 11, 2018

(54) ***WOLFFIA* PLANT NAMED 'MANKAI'**

(50) Latin Name: *Wolffia Globosa*
Varietal Denomination: MANKAI

(71) Applicants: Hinoman Ltd., Or Yehuda (IL); Jacob Hai, DN Gilboa (IL)

(72) Inventor: Jacob Hai, DN Gilboa (IL)

(73) Assignees: Hinoman Ltd., Or Yehuda (IL); Jacob Hai, Giboa (IL)

( * ) Notice: Subject to any disclaimer, the term of this patent is extended or adjusted under 35 U.S.C. 154(b) by 114 days.

(21) Appl. No.: 15/330,249

(22) Filed: Aug. 30, 2016

(65) Prior Publication Data

US 2018/0064012 P1 Mar. 1, 2018

(51) Int. Cl.
*A01H 5/12* (2018.01)
*A01H 11/00* (2006.01)

(52) U.S. Cl.
USPC ..... Plt./342
CPC ..... *A01H 11/00* (2013.01)

(58) Field of Classification Search
USPC ..... Plt./342
See application file for complete search history.

(56) References Cited

PUBLICATIONS

"Hinoman Reveals the Smallest Veggie Protein," PR Newswire Association LLC, Jun. 29, 2015, http://www.prnewswire.com/news-releases/hinoman-reveals-the-smallest-veggie-protein-510622171.html, pp. 1-3 (Year: 2015).*

"Hinoman launches Mankai", ingredientsnetwork.com, UBM—Corporate, Jul. 1, 2015, http://www.ingredientsnetwork.com/hinoman-launches-mankai-news037161.html, 3 pages.

"Hinoman Reveals the Smallest Veggie Protein", PR Newswire, PR Newswire Association LLC, Jun. 29, 2015, http://www.prnewswire.com/news-releases/hinoman-reveals-the-smallest-veggie-protein-510622171.html, 3 pages.

"Hinoman's Vegetable Whole-protein Ingredient Granted GRAS Status", Food Law Latest, WordPress.com, Aug. 3, 2015, https://foodlawlatest.com/tag/mankai/, 9 pages.

"Hinoman's Vegetable Whole-protein Ingredient Granted GRAS Status", PR Newswire, PR Newswire Association LLC, Aug. 3, 2015, http://www.prnewswire.com/news-releases/hinomans-vegetable-whole-protein-ingredient-granted-gras-status-300122346.html, 3 pages.

Press, Viva Sarah, "Hinoman announces world's smallest veggie protein—Mankai", ISRAEL21c, Israel21c, Jul. 1, 2015, http://www.israel21c.org/hinoman-announces-worlds-smallest-veggie-protein-mankai/, 2 pages.

Watson, Elaine, "Tiny plants with huge potential: Introducing two new players to the plant-based protein market", FOODnavigator-usa.com, William Reed Business Media Ltd., Aug. 3, 2015, http://www.foodnavigator-usa.com/R-D/Tiny-plants-with-huge-potential-Introducing-LENTEIN-Plus-and-mankai, 6 pages.

Watson, Elaine, "Ultra-fast-growing aquatic plant promises year-round supply of sustainable vegetable protein", FOODnavigator-usa.com, William Reed Business Media Ltd., Jul. 6, 2015, http://www.foodnavigator-usa.com/Suppliers2/Aquatic-plant-promises-year-round-supply-of-sustainable-plant-protein, 6 pages.

* cited by examiner

*Primary Examiner* — Anne Marie Grunberg
(74) *Attorney, Agent, or Firm* — The Webb Law Firm

(57) ABSTRACT

A new and distinct *Wolffia Globosa* plant that exhibits fast vegetative propagation, an ovoid shape, and is neutral in taste.

11 Drawing Sheets

Botanical classification: *Wolffia Globosa.*
Varietal denomination: 'MANKAI'.

BACKGROUND OF THE INVENTION

The present invention comprises a new and distinct *Wolffia Globosa* variety known by the varietal name 'MANKAI'. 'MANKAI' was derived from an unnamed and unpatented *Wolffia globosa* variety originating from Ramat Ha'Golan, Israel that was placed in a cultivated area of a controlled water growth medium having a pH range between 4-11 and water temperature range between 17-30° C., with continuous low movement, aeration, and fertilization being provided in Moshav Merhavia, Israel. After a period of a forced selection process and observation, 'MANKAI' was discovered and selected in said cultivated area as an improved *Wolffia globosa* variety by the inventor in 2005. When compared to an unnamed and unpatented *Wolffia Globosa* variety known to the breeder, 'MANKAI' exhibits a similar vegetative propagation rate, but the unnamed variety has a round shape, differs in length, and is light green in color. The new variety has been trialed and tested and has been found to retain its distinctive characteristics and remain true to type through successive propagations.

The parental plant and 'Mankai' are similar in vegetative propagation rates, however 'Mankai' differs from its parent plant in that the parent plant is round and 0.5 mm-1 mm in length, whereas 'Mankai' is ovoid and 0.4 mm-0.85 mm in length. In addition, the parental type is lighter green in color compared to 'Mankai'.

The following characteristics distinguish the new variety from other *Wolffia Globosa* varieties known to the breeder:

1. Ovoid shape;
2. Length of 0.4-0.85 mm and width of 0.3-0.65 mm;
3. Fast vegetative propagation—8 to 9 times over a period of 16 to 19 days before dying as a white frond devoid of any further daughter fronds within it;
4. Neutral taste;
5. Dry biomass of 4-5%; and
6. Green (7490C) color.

DESCRIPTION OF THE DRAWINGS

The accompanying photographic drawings illustrate the new cultivar, with the color being as nearly true as is possible with color illustrations of this type.

DESCRIPTION OF THE NEW VARIETY

Figure 1:
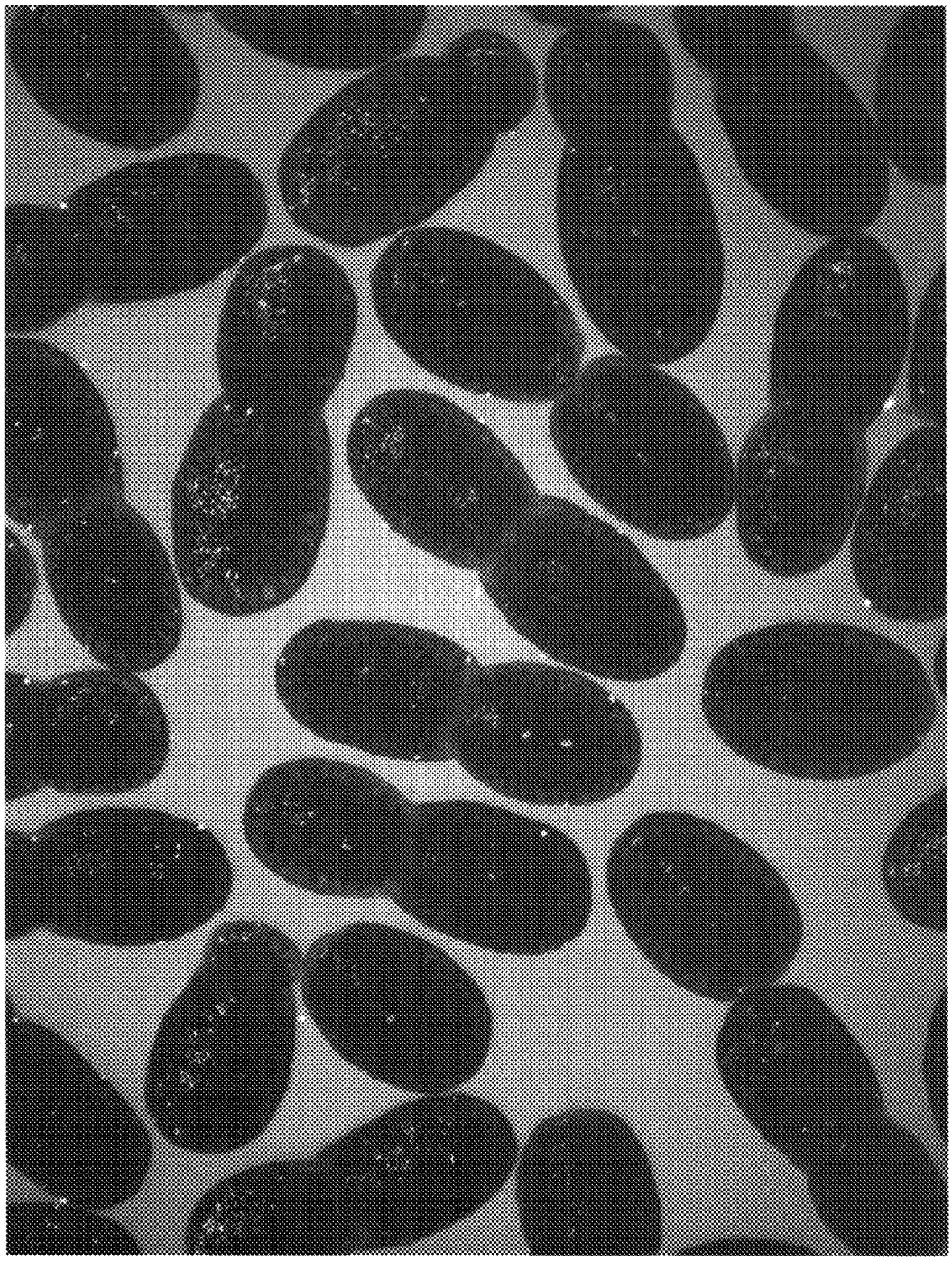
FIG. 1 illustrates a population of plants of the new variety in log phase. The image was photographed with a Micros Cam 500 attached to a stereoscopic binocular microscope (Ladybird MZ1240) with lighting from above and below. The level of objective magnification is 45×.
Figure 2:
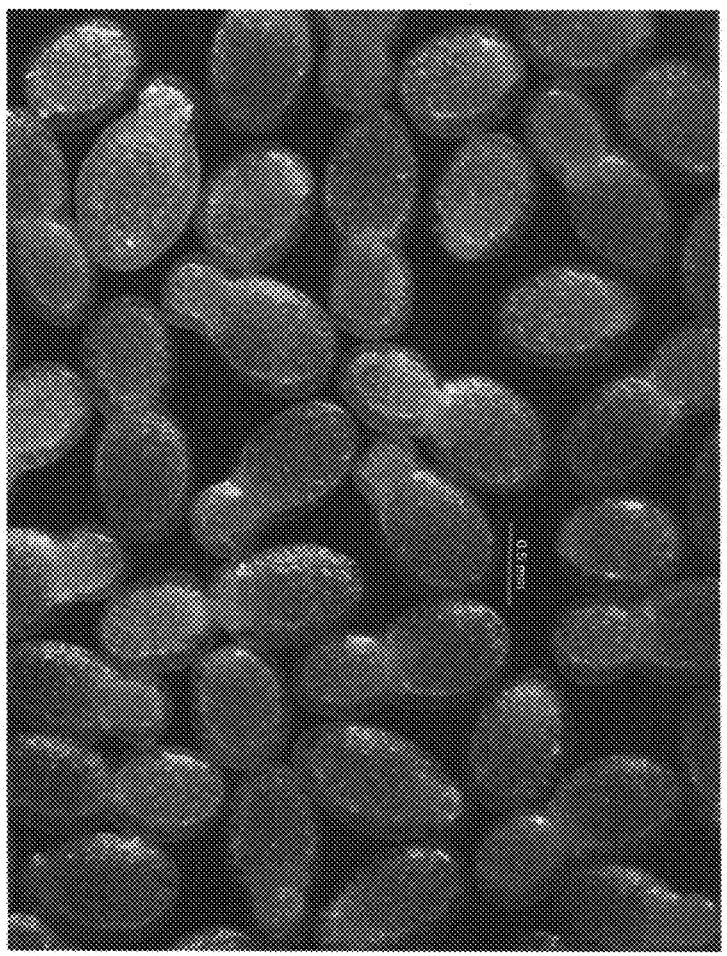
FIG. 2 illustrates a non-synchronous population of plants in mid-log phase. 30 of 36 fronds are at some stage of budding, from incipient emergence of a daughter frond to almost complete separation of a mother and daughter frond. The size ranges of budding mother fronds are 0.6-0.8 mm in length and 0.5-0.6 mm in width. The variation in size is due to the growth cycle of a mother frond, which typically births 8-9 daughter fronds in its life time: a first-time mother reaches 0.6 mm in length, a third to eighth time mother reaches 0.8 mm in length. The widths are proportionate to the lengths. The image was photographed with a Nikon SMZ 1500 stereo microscope with lighting from above.
Figure 3:
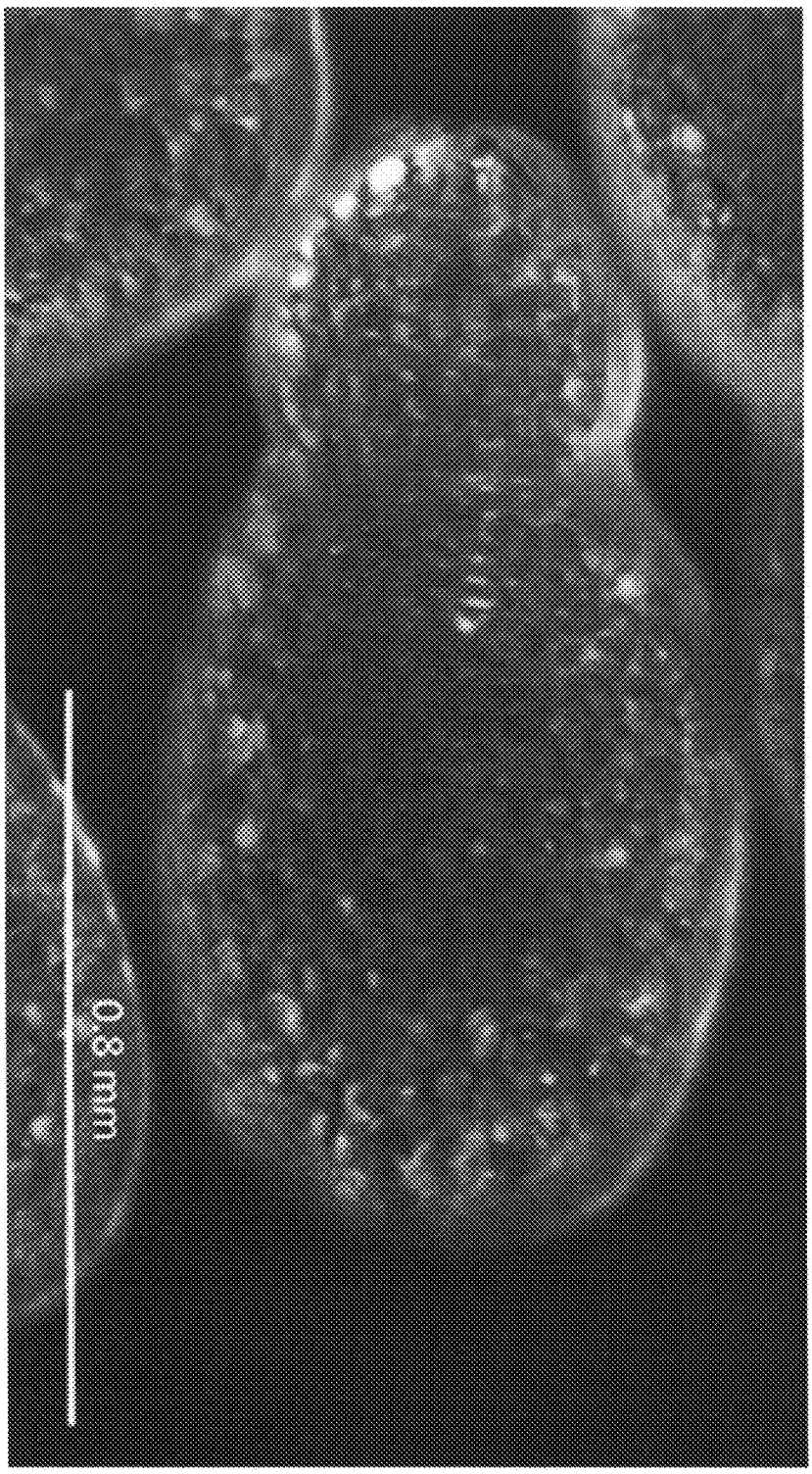
FIG. 3 illustrates a single mature plant of the new variety.
Figure 4:
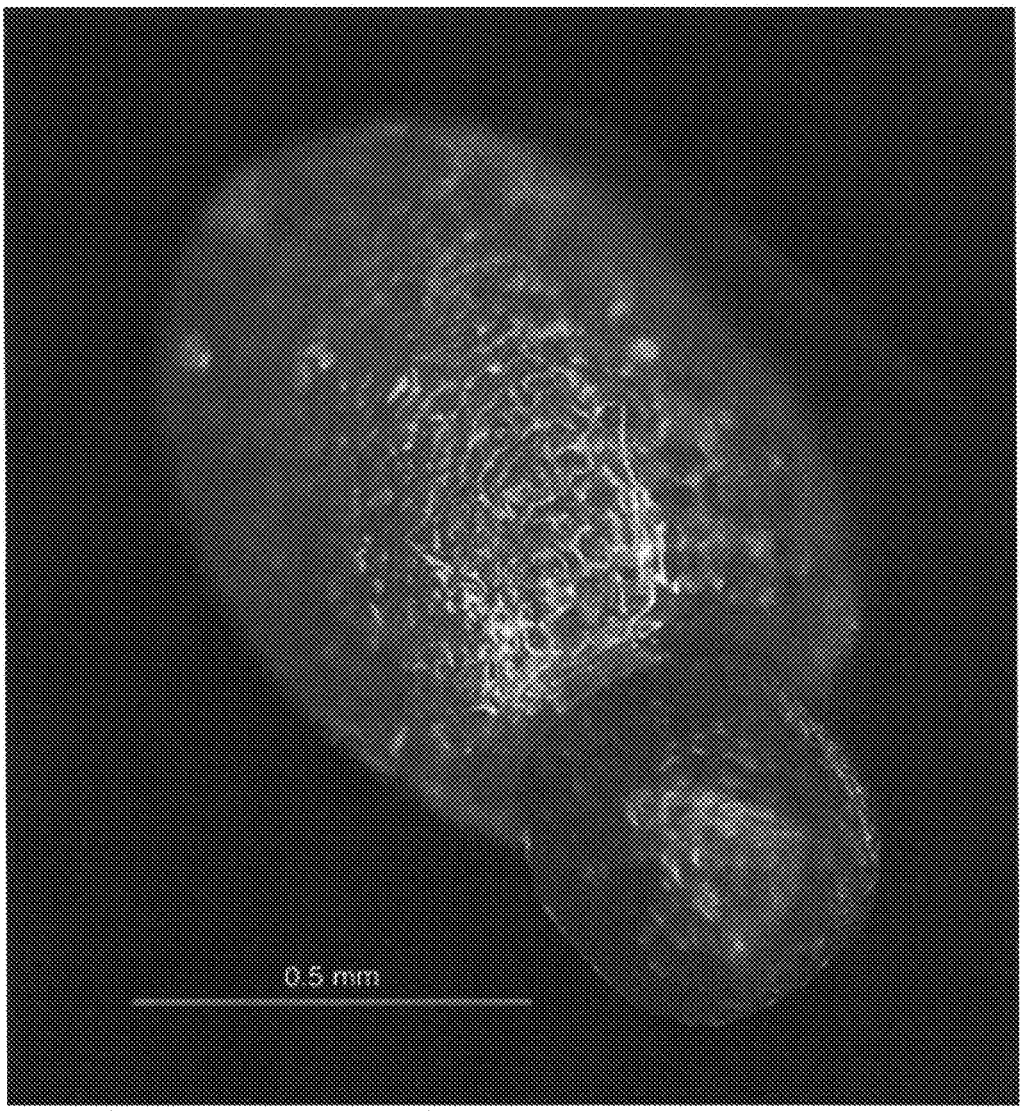
FIG. 4 illustrates a close up, dorsal view of a budding plant of the new variety with the dorsal face floating at the water line. The mother frond is birthing a daughter frond, with the meristematic pouch decorated with characteristic concentric lines of elongated cells at the mouth of the pouch. The image was photographed with a Nikon SMZ18 stereoscopic binocular microscope using a Nikon DS-RI1 camera with lighting from above. The magnification was provided by the 0.5 mm bar. The length of the mature mother frond is 0.8 mm and the width is 0.55 mm
Figure 5:
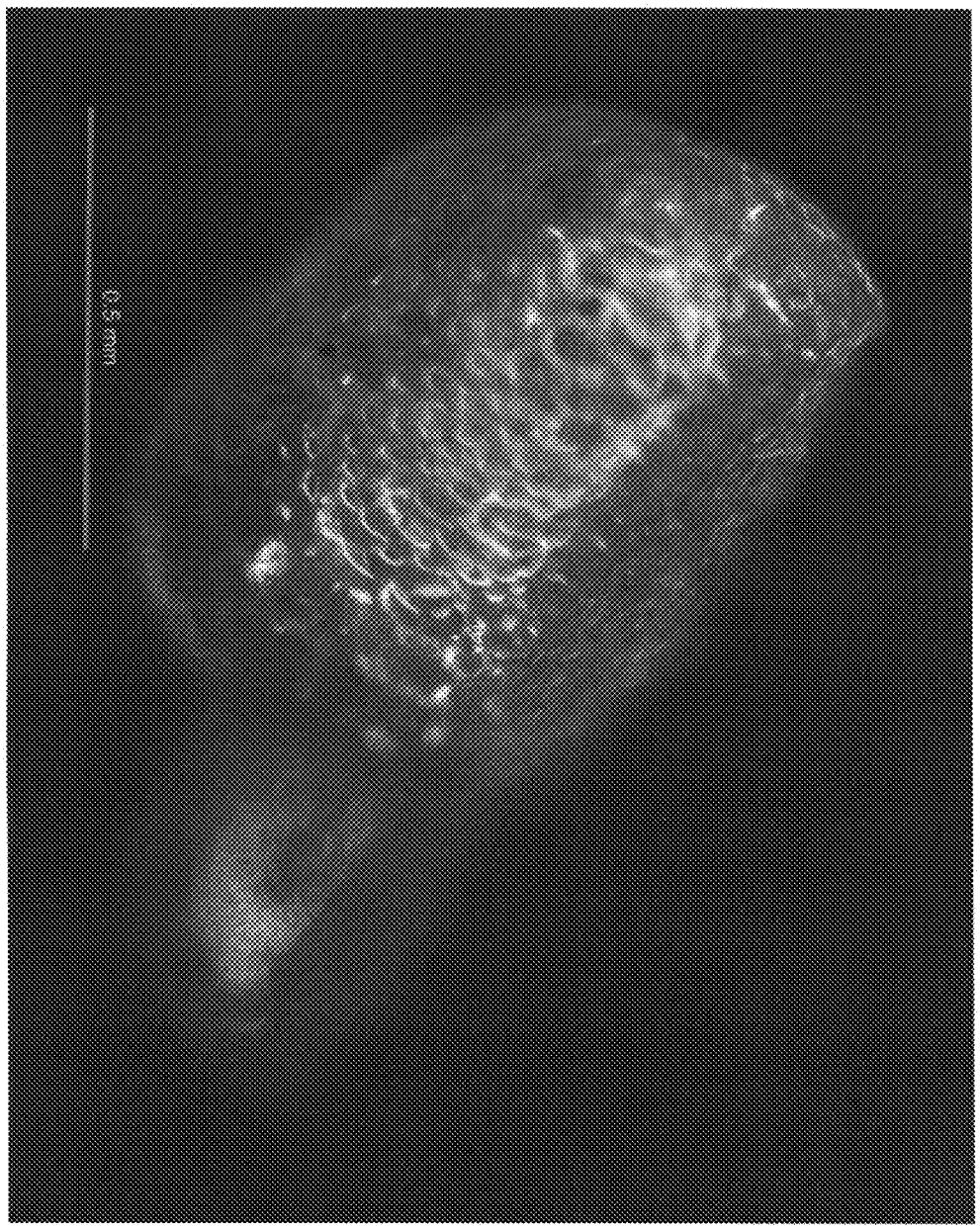
FIG. 5 illustrates a close up, side view of a budding plant of a mother frond of the new variety that reveals the green, photosynthetic, almost flat, dorsal face at the surface of the water and the diminishingly-green submerged body. The emerging daughter frond appears green throughout. The image was photographed with a Nikon SMZ18 stereoscopic binocular microscope using a Nikon DS-RI1 camera with lighting from above. The magnification was provided by the 0.5 mm bar. The length of the mature mother frond is 0.8 mm and the depth (height) is 0.7 mm.
Figure 6:
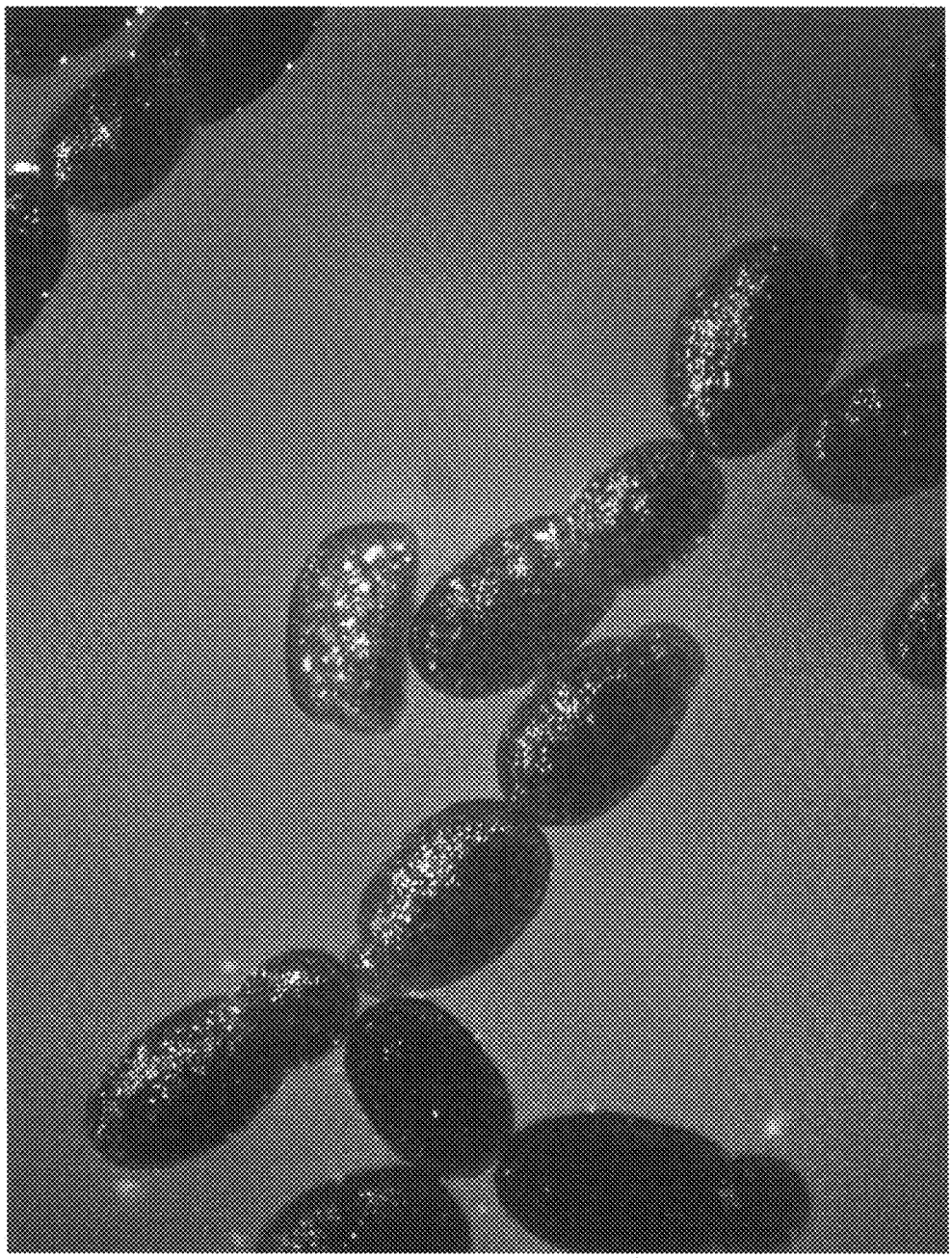
FIG. 6 illustrates a population of plants of the new variety, with one plant shown in side view. The image was photographed with a Micros Cam 500 attached to a stereoscopic binocular microscope Ladybird MZ1240 with lighting from above and below. The level of objective magnification is 45×.
Figure 6A:
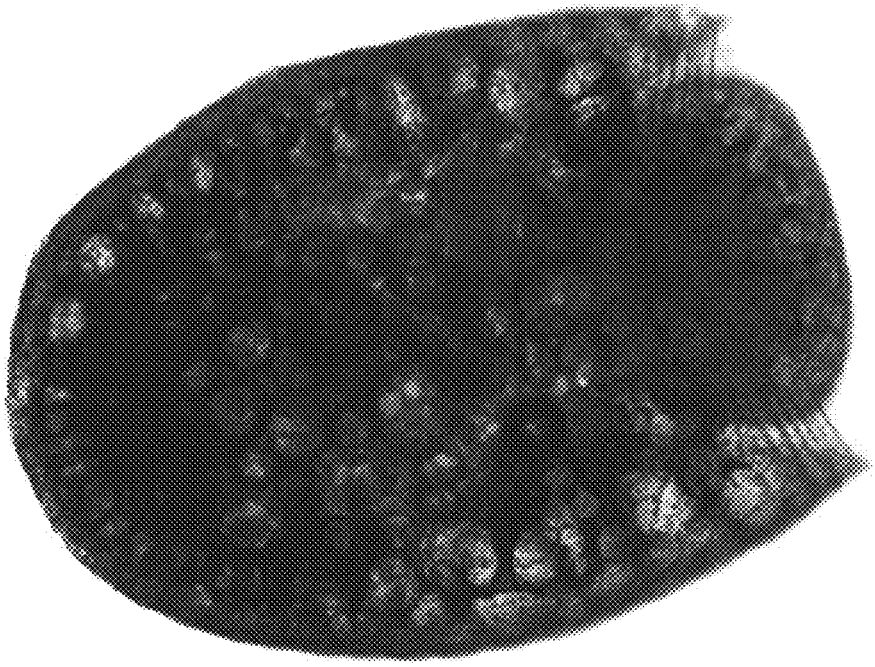
FIG. 6*a* illustrates a new frond appearing from a mother frond of the new variety. The image was photographed with a Micros Cam 500 attached to a light microscope (Bresser Art. No. 57-23100). The level of objective magnification is 10×.
Figure 7:
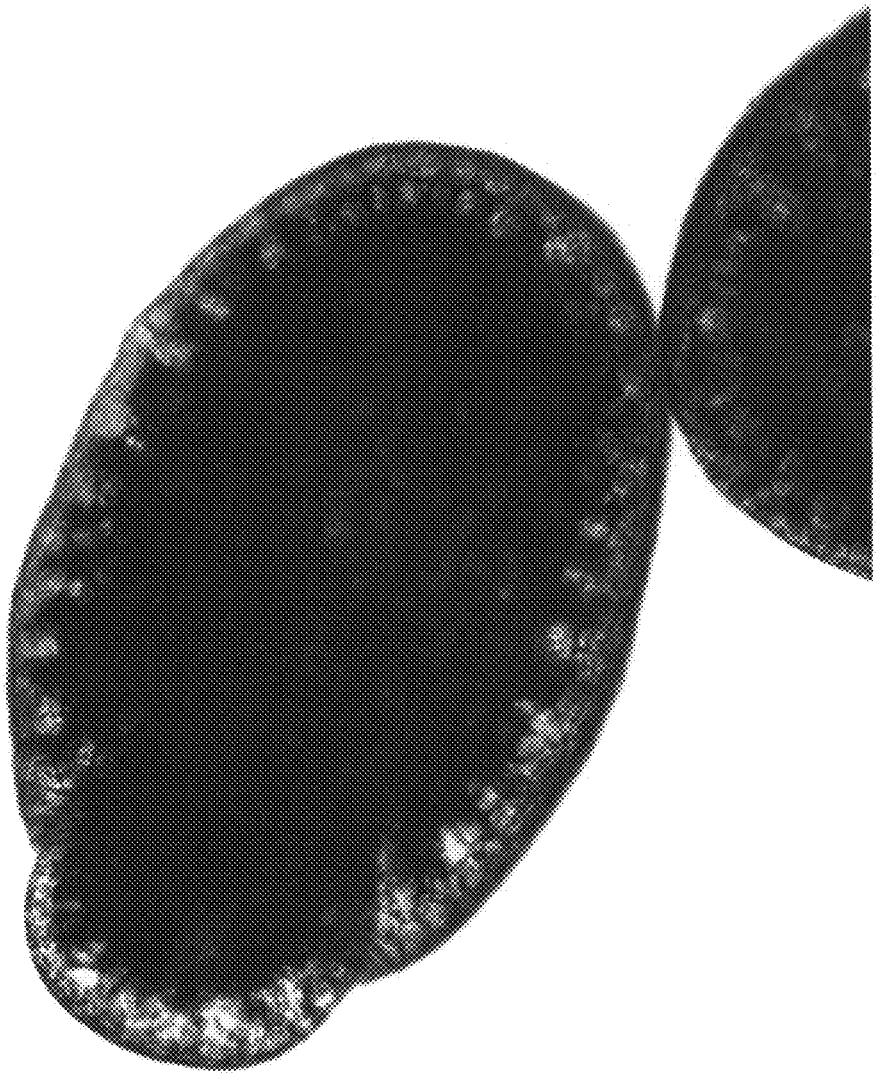
FIG. 7 illustrates a mother frond with a daughter frond of the new variety. The image was photographed with a Micros Cam 500 attached to a light microscope (Bresser Art. No. 57-23100). The level of objective magnification is 10×.
Figure 8:
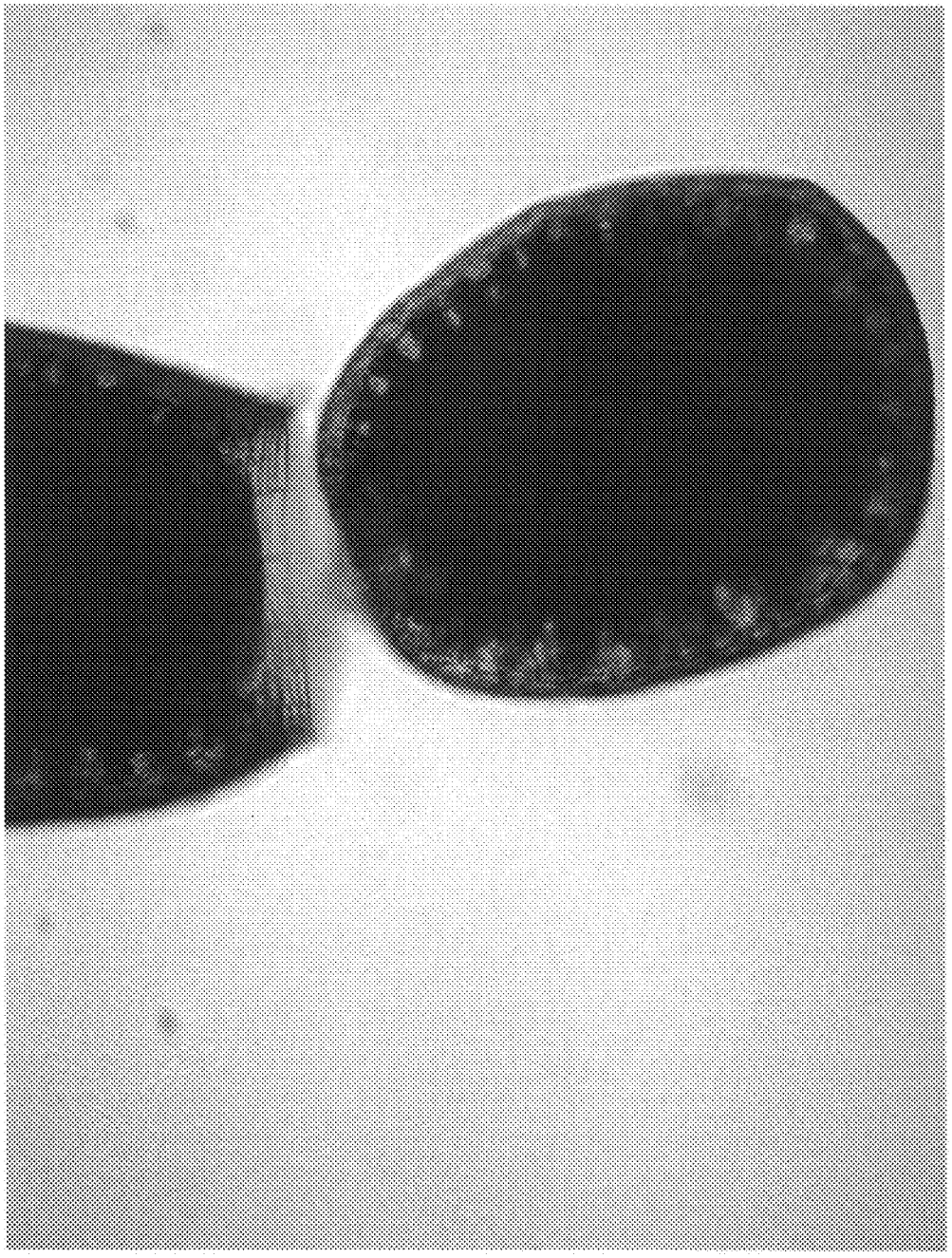
FIG. 8 illustrates a new frond of the present variety. The image was photographed with a Micros Cam 500 attached to a light microscope (Bresser Art. No. 57-23100). The level of objective magnification is 10×.
Figure 9:
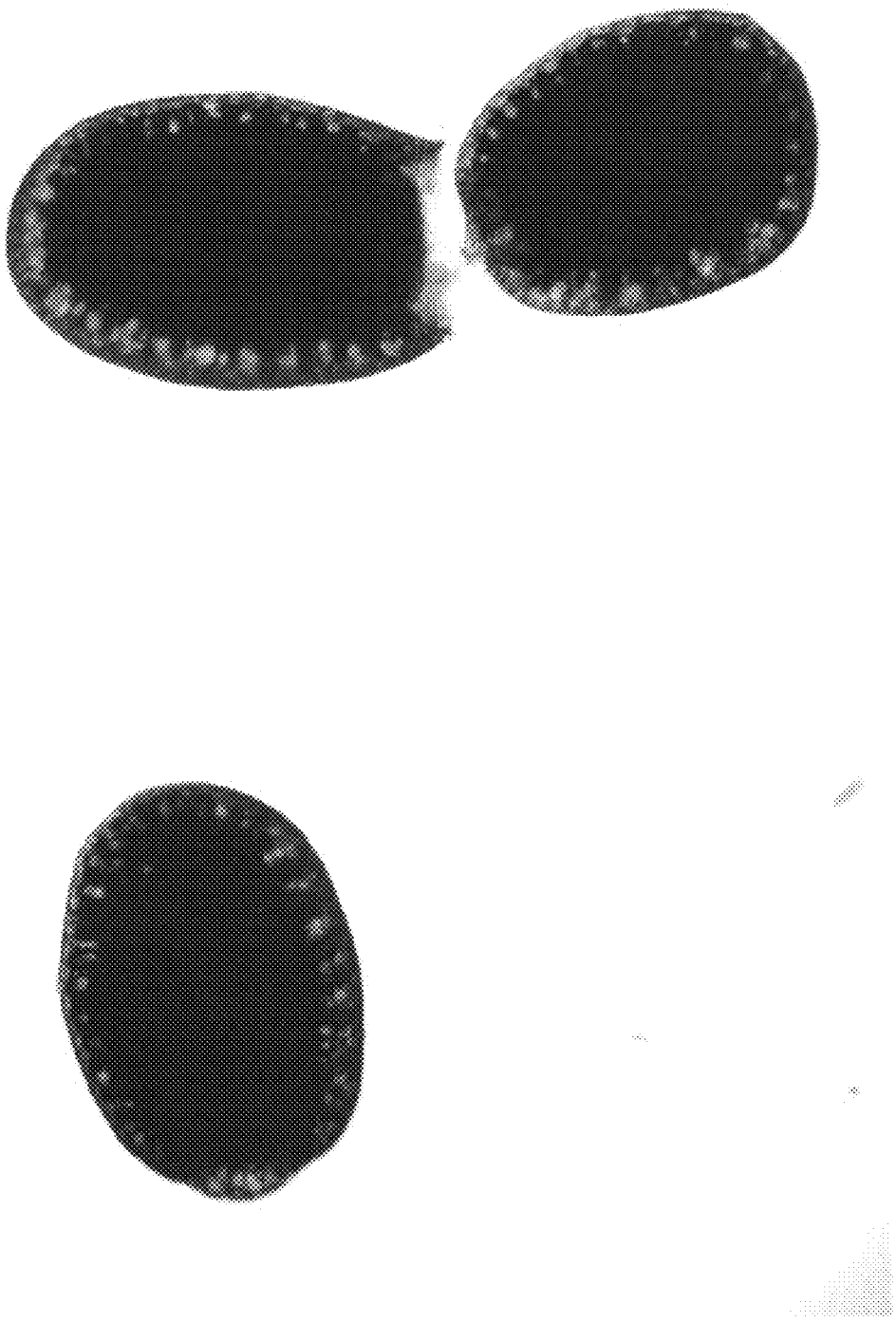
FIG. 9 illustrates young fronds of the new variety. The image was photographed with a Micros Cam 500 attached to a light microscope (Bresser Art. No. 57-23100). The level of objective magnification is 4×.
Figure 9A:
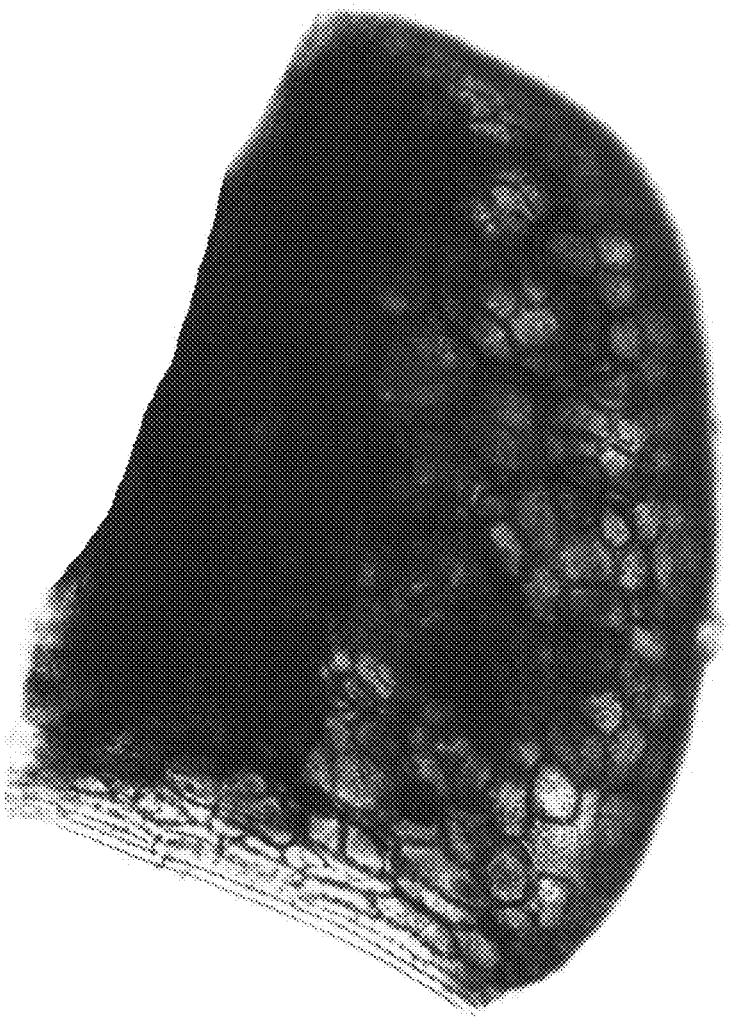
FIG. 9*a* illustrates an open pouch of the new variety. The image was photographed with a Micros Cam 500 attached to a light microscope (Bresser Art. No. 57-23100). The level of objective magnification is 10×.

The following detailed description sets forth the characteristics of the new variety. The data which defines these characteristics are the result of asexual reproductions first carried out by budding in 2005 in Moshav Merhavia, Israel. The new variety was grown in a water medium at room temperatures under continuous low movement, with aeration, and fertilization provided. If the electrical conductivity was measured higher than 1.8 mS, the culture medium was refreshed. The location where the variety was described at an age of log stage growth was in Moshav Dekel, Israel under cool LED lighting with an intensity of 160 μE $m^{-2}$ $s^{-1}$. Color references are primarily from the Pantone Catalogue—The Plus Series 2016.

PLANT

Time to produce a finished plant: About 4-5 days at about 25° C.

Description of the plant's multiplication habit: Fast vegetative propagation of 8 to 9 times over a period of 16 to 19 days before dying as a white frond devoid of any further daughter fronds within it.

Body description: Frond without veins having one funnel-shaped budding pouch at the basal end. The clonal clusters are either solitary or two-connected. The dorsal surface is rounded on the edges with and the upper central portion is flattened. The floating variety shows only a central portion of its dorsal surface above water. No brown epidermal pigment cells are present. The new variety has a distinct translucent edge.

Shape: Ovoid.

Length: 0.4-0.85 mm.

Diameter: 0.4-0.6 mm.

Young plant color: Green (7490C).

Mature plant color: Green (7490C).

Stomata number: Less than 20.

Flower description: None observed.

Disease/pathogen resistance: None observed.

Temperature tolerance: 30° C. of water media and 40° C. of the air.

Drought tolerance: None.

Use: As an addition to different kinds of food products in fresh, frozen, or dried form.

The following TABLE 1 illustrates the biomass doubling time of the new variety:

TABLE 1

| SIZE | COLOR | BIOMASS DOUBLING TIME (Days) | NOTES |
|---|---|---|---|
| 0.5 mm | Green | 3-3.5 | Green, 1 day lag before division. |
| 0.6 mm | Green | 2-2.5 | Green, small, rapid division. |
| 0.8 mm | Green | 2-2.5 | Green, full sized, rapid division. |

TABLE 1-continued

| SIZE | COLOR | BIOMASS DOUBLING TIME (Days) | NOTES |
|---|---|---|---|
| 0.8 mm | Light green | 3-5 | Losing color, full sized, slower division. |
| 0.9 mm | None | None | Colorless, bloated size with age, no division. |

The nutritional value of the new variety is illustrated in the additional tables below:

TABLE 2

| General Composition | % |
|---|---|
| Protein | 45.79 |
| Ash | 15.28 |
| Carbohydrates | 27.54 |
| Moisture | 4.9 |
| Fat as Triglycerides | 6.49 |
| Saturated Fat | 1.33 |
| Polyunsaturated Fat | 4.48 |
| Monounsaturated Fat | 0.38 |
| Total Fatty Acids | 6.2 |
| Total Omega 3 isomers | 3.46 |
| Total Omega 6 isomers | 1.01 |
| Total Omega 9 isomers | 0.08 |
| Cholesterol | 0 |
| Dietary Fiber, total | 23.3 |
| Calories from Fat, [kcal] | 58 |
| Calories, [kcal] | 352 |

TABLE 3

| Minerals | mg/kg |
|---|---|
| Calcium (Ca) | 6410 |
| Magnesium (Mg) | 2440 |
| Iron (Fe) | 272 |
| Sodium (Na) | 1400 |
| Phosphorus (P) | 18400 |
| Zinc (Zn) | 158 |
| Selenium (Se) | 0.16 |

TABLE 4

| Amino Acids | % |
|---|---|
| Tryptophan | 0.91 |
| Cystine | 0.48 |
| Methionine | 0.7 |
| Aspartic acid | 3.72 |
| Threonine | 1.85 |
| Serine | 1.8 |
| Glutamic acid | 4.47 |
| Proline | 1.77 |
| Glycine | 2.04 |
| Alanine | 2.39 |
| Valine | 2.27 |
| Isoleucine | 1.7 |
| Leucine | 3.28 |
| Tyrosine | 1.36 |
| Phenylalanine | 2.28 |
| Total Lysine | 3.06 |
| Histidine | 0.91 |
| Arginine | 4.2 |

TABLE 5

| Vitamins | mg/100 g |
|---|---|
| beta-carotene | 45.41 |
| Lutein | 72.5 |
| Zeaxanthin | 13 |
| Vitamin A (RAE) | 3.785 |
| Biotin (Vitamin 7) | 0.087 |
| Vitamin B1 (Thiamine HCl) | 1.05 |
| Vitamin B2 (Riboflavin) | 3.24 |
| Vitamin B3 (Niacin) | 16.3 |
| Vitamin B5 (Pantothenic Acid) | 3.49 |
| Vitamin C | 99.4 |
| Vitamin E (Tocopherols) | 48.4 |
| Vitamin K | 0.293 |
| Vitamin B6 (pyridoxine) | 0.704 |
| Folic acid, total | 3.08 |
| Choline, total | 239 |

I claim:

1. A new and distinct variety of *Wolffia Globosa* plant substantially as shown and described herein.

* * * * *